(12) United States Patent
Wilson (10) Patent No.: US 8,394,386 B2
(45) Date of Patent: Mar. 12, 2013

(54) SEQUENTIAL DELIVERY OF IMMUNOGENIC MOLECULES VIA ADENOVIRUS AND ADENO-ASSOCIATED VIRUS-MEDIATED ADMINISTRATIONS

(75) Inventor: James M. Wilson, Glen Mills, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1707 days.

(21) Appl. No.: 11/587,543

(22) PCT Filed: Apr. 27, 2005

(86) PCT No.: PCT/US2005/014556
§ 371 (c)(1),
(2), (4) Date: Oct. 25, 2006

(87) PCT Pub. No.: WO2006/078279
PCT Pub. Date: Jul. 27, 2006

(65) Prior Publication Data
US 2008/0241189 A1    Oct. 2, 2008

Related U.S. Application Data

(60) Provisional application No. 60/565,936, filed on Apr. 28, 2004.

(51) Int. Cl.
*A61K 39/23* (2006.01)
*A61K 39/116* (2006.01)
*C12Q 1/70* (2006.01)

(52) U.S. Cl. ........................ 424/233.1; 435/5; 424/203.1

(58) Field of Classification Search ................ None
See application file for complete search history.

(56) References Cited

U.S. PATENT DOCUMENTS

| | | |
|---|---|---|
| 5,856,152 A | 1/1999 | Wilson |
| 5,866,552 A | 2/1999 | Wilson |
| 5,871,982 A | 2/1999 | Wilson |
| 6,001,557 A | 12/1999 | Wilson |
| 6,083,716 A | 7/2000 | Wilson |
| 6,203,975 B1 | 3/2001 | Wilson |
| 6,251,677 B1 | 6/2001 | Wilson |
| 6,387,368 B1 | 5/2002 | Wilson |
| 6,759,237 B1 | 7/2004 | Wilson |
| 7,105,345 B2 | 9/2006 | Wilson |
| 7,261,882 B2* | 8/2007 | Watkins ................ 424/85.2 |
| 2003/0138772 A1 | 7/2003 | Gao et al. |
| 2003/0228282 A1 | 12/2003 | Gao et al. |
| 2004/0057931 A1 | 3/2004 | Wilson |
| 2004/0057933 A1 | 3/2004 | Wilson |
| 2004/0136963 A1 | 7/2004 | Wilson |
| 2005/0069866 A1 | 3/2005 | Wilson |
| 2006/0204479 A1 | 9/2006 | Wilson |
| 2006/0216272 A1* | 9/2006 | Emini et al. ................ 424/93.2 |
| 2009/0175910 A1* | 7/2009 | Nabel et al. ................ 424/208.1 |

FOREIGN PATENT DOCUMENTS

| | | |
|---|---|---|
| WO | WO 96/13597 A3 | 5/1996 |
| WO | WO 96/13598 A2 | 5/1996 |
| WO | WO 98/09657 A2 | 3/1998 |
| WO | WO 98/10087 A1 | 3/1998 |
| WO | WO 00/28061 A3 | 5/2000 |
| WO | WO 00/76539 A2 | 12/2000 |
| WO | WO 03/042397 A2 | 5/2003 |
| WO | WO 03/046124 A2 | 6/2003 |
| WO | WO 03/052051 A2 | 6/2003 |
| WO | WO 03/077859 A | 9/2003 |
| WO | WO 2005/033321 A2 | 4/2005 |

OTHER PUBLICATIONS

Mizuguchi et al In vitro ligation-based cloning of foreign DNAs into the E3 and E1 deletion regions for generation of recombinant adenovirus vectors. Biotechniques. May 2001;30(5):1112-4, 1116.*
Farina et al. Replication-defective vector based on a chimpanzee adenovirus. J Virol. Dec. 2001;75(23):11603-13.*
van der Burg et al. Pre-clinical safety and efficacy of TA-CIN, a recombinant HPV16 L2E6E7 fusion protein vaccine, in homologous and heterologous prime-boost regimens. Vaccine. Jun. 14, 2001;19(27):3652-60.*
Warrington et al. Adeno-associated virus type 2 VP2 capsid protein is nonessential and can tolerate large peptide insertions at its N terminus. J Virol. Jun. 2004;78(12):6595-609.*
Ponnazhagan S. Adenoassociated virus vectors for genetic immunization. Immunol Res. 2002;26(1-3):247-53.*
Russell, Update on Adenovirus and its Vectors, Journal of General Virology, 81, pp. 2573-2604, (Aug. 2000).
Jooss et al, Transduction of Dendritic Cells by DNA Viral Vectors Directs the Immune Response to Transgene Products in Muscle Fibers, Journal of Virology, vol. 72, No. 5, pp. 4212-4223, (May 1998).
Zhi et al, Increased Antigen-Specific Humoral Response by Adenoviral Vector Prime and Adeno-Associated Viral Vector Boost, Molecular Therapy, Academic Press, San Diego, Ca, vol. 9, p. 214, (May 2004).
Gilbert et al, Enhanced CD8 T Cell Immunogenicity and Protective Efficacy in a Mouse Malaria Model Using a Recombinant Adenoviral Vaccine in Heterologous Prime-Boost Immunization Regimes, Vaccine Butterworth Scientific, Guildford, GB, vol. 20, No. 7-8, pp. 1039-1045, (Jan. 15, 2002).
Jooss et al, Immunity to Adenovirus and Adeno-associated Viral Vectors: Implications for Gene Therapy, Gene Therapy, vol. 10, No. 11, pp. 955-963, (Jun. 2003).
Park et al, Efficient Induction of T Helper 1 CD4<+> T-Cell Responses to Hepatitis C Virus Core and E2 by a DNA Prime-Adenovirus Boost, Vaccine, Butterworth Scientific, Guildford, GB, vol. 21, No. 31, pp. 4555-4564, (Nov. 7, 2003).
English-language translation of Jan. 25, 2011 Office Action in counterpart Japanese Patent Application No. 2007-510962 (citing PCT-WO 00/76539-A2 (Document "F1" herein) and Gilbert 2002.
Fields, et al., Role of Vector in Activation of T Cell Subsets in Immune Responses against the Secreted Trangene Product Factor IX, Molecular Therapy, Mar. 2000, 3(1):225-235.

(Continued)

*Primary Examiner* — Michele K Joike
(74) *Attorney, Agent, or Firm* — Howson & Howson LLP (57) ABSTRACT

An immunogenic regimen is provided. The regimen involves sequential administration of a recombinant adenoviral vector and a recombinant adeno-associated viral vector, each of which delivers a heterologous expression cassette encoding the same immunogenic product, or a cross-reactive immunogenic product. Also provided are products containing the vectors for use in the regimen of the invention.

23 Claims, 1 Drawing Sheet

OTHER PUBLICATIONS

Lin, Jianping, et al., a New Genetic Vaccine Platform Based on an Adeno-Associated Virus Isolated from a Rhesus Macaque, Journal of Virology, Oct. 7, 2009 (online), 83(24):12738-12750.

Lin, Jianping, et al., Vaccines Based on Novel Adeno-Associated Virus Vectors Elicit Aberrant CD8+ T-Cell Responses in Mice, Journal of Virology, Aug. 22, 2007 (online), 81(21):11840-11849.

Lin, Shih-Wen, et al., Recombinant adeno-associated virus vectors induce functionally impaired transgene product-specific CD8+ T cells in mice, The Journal of Clinical Investigation, Nov. 15, 2007 (online), 117(12):3958-3970.

Instructions to Japanese agent (including claims) for response to Jan. 25, 2011 Office Action in counterpart Japanese Patent Application No. 2007-510962.

Sep. 27, 2011 Notice of Reasons for Rejection in counterpart Japanese Patent Application No. 2007-510962.

Instructions to Japanese agent (including claims and Declaration) for response to Sep. 27, 2011 Notice of Reasons for Rejection in counterpart Japanese Patent Application No. 2007-510962.

Certified Final Rejection (English-language translation)—May 29, 2012—in counterpart Japanese Patent Application No. 2007-510962.

Feb. 8, 2012 Office Action in counterpart Canadian Patent Application No. 2,563,538.

\* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: H-2k restricted eboZ GP-specific peptide

<400> SEQUENCE: 1

Thr Glu Leu Arg Thr Phe Ser Ile
1               5
```

US 8,394,386 B2

SEQUENTIAL DELIVERY OF IMMUNOGENIC MOLECULES VIA ADENOVIRUS AND ADENO-ASSOCIATED VIRUS-MEDIATED ADMINISTRATIONS

CROSS-REFERENCE TO RELATED APPLICATIONS

This is a national stage application under 35 U.S.C. 371 of PCT/US05/014556, filed Apr. 27, 2005 which claims the benefit under 35 U.S.C. 119(e) of the priority of U.S. Patent Application No. 60/565,936, filed Apr. 28, 2004.

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA having inverted terminal repeats (ITRs), with a terminal protein attached covalently to the 5' termini. The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Recombinant adenoviruses have been described for delivery of molecules to host cells to induce an immune response. See, U.S. Pat. No. 6,083,716, which provides adenoviral vectors derived from the two chimpanzee adenoviruses, C1 and C68 (also termed Pan 9) and International Patent Publication No. WO 02/33645 [Pan 5, Pan6, Pan7-derived vectors].

What is needed in the vaccine field is method of immunizing that will induce a strong immune response with minimal responses to the vaccine carrier.

SUMMARY OF THE INVENTION

The methods of the invention involve sequentially delivering one or more selected heterologous gene(s) to a mammalian patient via an adenoviral vector and an adeno-associated virus vector. Each of the vectors expresses the same immunogenic or antigenic product or a cross-reactive product.

The method of the invention provides a boosting of the immune response to the product carried by the viral vectors.

These and other embodiments and advantages of the invention are described in more detail below.

BRIEF DESCRIPTION OF THE DRAWINGS

FIG. 1 illustrates the total IgG responses to EboZ GP after heterologous prime and boost. B10Br mice were IM immunized with $5\times10^{10}$, $5\times10^{9}$, or $5\times10^{8}$ particles/mouse of H5GP vector. Six weeks later, mice were boosted IM with $5\times10^{10}$ genome copies/mouse of AAV2/1 GP vector. Serum from 3 mice in each group were collected and pooled at either day 42 after injection (pre-boost), or 1 week after boost, or 2 weeks after boost, as indicated in the FIGURE. Total IgG responses to GP were measured by ELISA.

DETAILED DESCRIPTION OF THE INVENTION

The invention provides a method of specifically inducing an immune response by administering an adeno-associated virus (AAV) vector and an adenoviral (Ad) vector. Each of the viral vectors contains a heterologous expression cassette comprising a nucleic acid sequence encoding a product for inducing an immune response under the control of regulatory control sequences which direct expression of the product. In one embodiment, the encoded products are the same in order to provide a prime/boost effect to the product, which induces immunity to the pathogen from which the product is derived or a cross-reactive pathogen. However, the regulatory control elements and other viral elements can differ in the adenoviruses administered. In another embodiment, the encoded products differ, but provide a cross-reactive effect.

Unexpectedly, the inventors have found that a significant antigen-specific humoral response is observed in a regimen involving sequential rAd-mediated and rAAV-mediated administration of the antigen. Without wishing to be bound by theory, it is believed that an enhanced T cell response may also be observed, depending upon the antigen and route of administration.

Thus, the method of the invention involves sequential administration of an adenoviral vector carrying a heterologous expression cassette and an AAV vector carrying a heterologous expression cassette, as described herein. As used herein, sequential administration encompasses delivery of an adenoviral vector followed by delivery of an AAV vector, i.e., at a time period apart from one another. Sequential administration further encompasses delivery of an AAV vector followed by delivery of an adenoviral vector. The method of the invention also encompasses coadministration of an adenoviral vector and an AAV vector, i.e., administration simultaneously or in close time proximity to each other, whether formulated together or separately. In one embodiment, sequential delivery of the antigenic product can be achieved even upon co-administration of different vectors due to the kinetics of antigen expression via one of the vectors, the use of an inducible promoter, or some other activatable expression system.

In one embodiment, the immunization regimen of the invention provides administration of multiple adenoviral vectors in combination with sequential administration of an AAV vector as described herein. In another embodiment, the regimen of the invention provides administration of an adenoviral vector in combination with sequential administration of multiple AAV vectors. In yet another embodiment, the regimen provides sequential administration of multiple adenoviral vectors in combination with multiple AAV vectors.

In the present invention, a regimen that involves administration of more than one adenoviral vector typically utilizes a first adenoviral vector having a capsid protein of a first serotype and administration of at least one additional adenoviral vector that has a capsid protein which is immunologically distinct from the prior adenoviral vector(s).

As used herein, a capsid protein is immunologically distinct from another capsid protein if it can be administered to a subject in the absence of an immune response which prevents infection with a second capsid protein (e.g., a clearing neutralizing antibody response). Suitably, the capsid proteins of a boosting vector(s) are from a serologically distinct source from the capsid protein of previously administered (priming) vector(s). However, in other embodiments, the capsid proteins of the priming (and optionally, boosting) vectors can be delivered without regard to serological distinctiveness, if the native antibody epitopes of the capsid proteins are masked, modified, or otherwise neutralized (e.g., by co-administration of an exogenous molecule).

Similarly, a regimen that involves administration of more than one AAV vector typically utilizes a first AAV vector having a capsid protein of a first serotype and administration of at least one additional AAV vector that has a capsid protein that is immunologically distinct from the prior AAV vector(s).

Depending upon the desired routes of administration, one of skill in the art can select an appropriate regimen. For example, peak immune response is generally observed about 10 to 14 days following an Ad-mediated delivery. However, boosting following this peak may generate a second peak. Thus, it may be desirable to time expression of a boosting antigen to express from about 10 to 21 days, or 18 to 28 days, or 28 days to 6 months following Ad-mediated delivery. In another example, certain AAV serotypes demonstrate peak expression about 3 to 4 weeks following delivery. Thus, boosting following AAV delivery may be timed to express the antigen, or a cross-reactive antigen, about 3 weeks to about 4 weeks, about 4 weeks to about 2 months, or about 2 months to 6 months, or longer, following AAV delivery.

In one embodiment, the heterologous expression cassette delivered via a viral vector, e.g., an AAV vector, according to the invention contains the immunogenic product operably linked to an inducible or regulatable promoter. When used in a regimen according to the present invention, the inducing or regulating agent is typically administered such that expression of product is activated immediately upon administration of the viral vector. Thereafter, expression can be extinguished by removal of the inducing or regulating agent. The regimen of the invention can include "pulse" activation of expression. Thus, the method of the invention permits expression to be induced, extinguished, and then again induced after a period of time. In another embodiment, expression is induced not upon administration, but several days to several weeks following administration. This embodiment may permit co-delivery of an Ad and AAV followed by induction (activation) several weeks following delivery, depending upon the delay caused by the induction agent. For example, once an inducing agent is delivered, it may be 7 to 10 days, or longer before the effect is observed. One of skill in the art will be familiar with the delay between delivery of the inducing or activating agent and the effect and will be able to readily factor this into the selected regimen.

Optionally, a regimen of the invention can be combined with administration of other immunogenic or therapeutic moieties including, e.g., DNA molecules encoding a desired immunogenic or therapeutic molecule, or a protein-based immunogen or therapeutic.

These and other aspect of the regimen of the invention, and the products of the invention, are described in more detail.

I. Adenoviral Vectors

The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

A. Serotypes

Suitably, the adenoviral vectors of the invention contain one or more adenoviral elements derived from a selected adenoviral genome. In one embodiment, the vectors contain adenoviral inverted terminal repeat (ITRs) from one selected serotype and additional adenoviral sequences from the same adenoviral serotype. In another embodiment, the vectors contain adenoviral sequences that are derived from a different adenoviral serotype than that which provides the ITRs. As defined herein, a pseudotyped adenovirus refers to an adenovirus in which the capsid protein of the adenovirus is from a different serotype than the serotype which provides the ITRs.

The selection of the serotype of the ITRs, any adenoviral genes present, the capsid protein, and the serotype of any other adenoviral sequences present in vector is not a limitation of the present invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Adenovirus vectors prepared from other simian or from human adenoviruses are described in the published literature [see, for example, U.S. Pat. No. 5,240,846]. The DNA sequences of a number of adenovirus types are available from the GenBank™ database, including type Ad5 [GenBank™ Accession No. M73260]. The adenovirus sequences may be obtained from any known adenovirus serotype, such as serotypes C, D, 1-40, and particularly 2, 3, 4, 5, 7, 12 and 40, and further including any of the presently identified human types. Similarly adenoviruses known to infect non-human animals (e.g., simians) may also be employed in the vector constructs of this invention. See, e.g., U.S. Pat. No. 6,083,716. Examples of other adenovirus serotype that may be useful in the method of the invention includes, e.g., serotype 34 [WO 2004/4097016], serotype 24 [WO 2004/083418]; and serotype 35 [EP 1054064].

The viral sequences, helper viruses, if needed, and recombinant viral particles, and other vector components and sequences employed in the construction of the vectors described herein are obtained as described above. The DNA sequences of the simian adenovirus sequences of the invention are employed to construct vectors and cell lines useful in the preparation of such vectors.

In one embodiment, at least one of the adenoviruses used in the invention contains a capsid derived from a non-human primate. Examples of suitable non-human primate sequences include simian adenoviruses, such as, Pan5 (also C5), Pan6 (also C6), Pan7 (also C7), SV1, SV25, SV39 [see, WO 02/33645, incorporated by reference], and Pan 9 (also C68) and C1 [U.S. Pat. No. 6,083,716, incorporated by reference], and SA 18 [U.S. patent application Ser. No. 10/465,302 and its international counterpart WO 2005/001103, incorporated by reference].

The invention further encompasses pseudotyped adenoviruses, chimeric and hybrid adenoviral vectors. See, e.g., U.S. patent application Ser. No. 10/465,302 and its international counterpart WO 2005/001103, incorporated by reference.

However, the invention is not limited to the selection of the capsid serotype or the origin of the other adenoviral elements present in the viral vector.

B. Adenoviral Elements

The adenoviral particles or vectors used in the present invention are composed of adenovirus capsids having packaged therein an expression cassette carrying a product to be expressed in the host and sufficient viral elements to permit delivery of the expression cassette to an infected host cell. These adenoviral vectors can be replication-defective, thereby avoiding replication in a host cell.

In one embodiment, adenoviral particles used in the invention contain 5' adenoviral cis-elements and 3' adenoviral cis-elements at the extreme 5' and 3' termini of the adenovirus, respectively. The 5' end of the adenoviral genome contains the 5' cis-elements necessary for packaging and replication; i.e., the 5' inverted terminal repeat (ITR) sequences (which functions as origins of replication) and the 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation.

The adenoviral vectors can contain functional adenoviral genes native to an adenoviral genome, or can contain multiple deletions relative to a native adenoviral genome. In one embodiment, the adenovirus has a functional deletion in the E1 region that renders it replication-defective and incapable of expressing the gene products of this region, including the E1a and E1b gene products.

In addition, the adenoviral vectors used in the invention can be functionally deleted in one or more of the other adenoviral early gene regions. For example, an adenoviral vector used in the invention can contain a functional deletion in the E1 region and, optionally, a functional deletion in one or more of the adenovirus E2 region, the adenovirus E3 region, or the adenovirus E4 gene region. Functional deletions in the E2 region may include destruction of the ability to express functional one or both of the E2 product, E2a and the E2b. Similarly, a functional deletion in the E4 region may include destruction of the ability to express functional ORF1, ORF2, ORF3, ORF4, ORF5, ORF6, ORF7 gene products.

Elimination of E3 permits insertion of an expression cassette in that region. However, E3 is believed to be implicated in modulation of host immune response to the adenovirus, and thus, in another embodiment, is retained. In this embodiment, the E3 gene product is expressed under the control of a heterologous promoter, to avoid down-regulation of the native E3 promoter which requires E1 expression.

The adenoviruses used in the invention that contain an E4-deletion are functionally deleted of one or more of the open reading frames (ORFs) of E4 (e.g., ORF 1, ORF2, ORF3, ORF4, ORF5, ORF6 and ORF7). In one embodiment, the construct contains a functional deletion of each of the E4 ORFs. In another embodiment, all E4 ORFs are deleted with the exception of E4 ORF6. In still another embodiment, another combination of one or more of these E4 ORFs is functionally deleted in the adenoviral construct used in the method of the invention.

An adenoviral vector used in the invention can be functionally deleted in one or more other adenoviral gene regions, e.g., in one or more of the adenoviral intermediate genes, genes IX and IVa$_2$, or adenoviral late genes (L1, L2, L3, L4 and L5).

In still other embodiments, other deletions may be made in the other structural or non-structural adenovirus genes. These deletions can be used individually, i.e., an adenovirus sequence for use in the present invention may contain deletions in only a single region.

Methods for generating adenoviral vectors containing functional deletions that eliminate the ability of the vector to express proteins required for packaging into an adenoviral capsid are known to those of skill in the art and are not a limitation of the present invention.

C. Vector Elements

The methods employed for the selection of the antigenic or immunogenic target (i.e., product) and the sequences encoding same, the cloning and construction of the "heterologous expression cassette" and its insertion into the viral vector are within the skill in the art given the teachings provided herein. According to the present invention, the heterologous expression cassette can be located in the site of any adenoviral region relative to a native adenoviral genome, which is located between the 5' and 3' adenovirus ITRs. In one embodiment, the heterologous expression cassette is located in the native E1 region of the adenoviral vector. In another embodiment, the heterologous expression cassette is located in the native E3 region. In other embodiments, the gene product is expressed from the native E2 region of the adenoviral vector or from the native E4 region of the adenoviral vector, and is operably linked to regulatory control elements which are non-contiguous with the sequences encoding the gene product. The invention is not limited to the orientation of the heterologous expression cassette, which may be inserted 5'-3' or 3'-5', relative the orientation of the adenoviral genome flanking the expression cassette.

In yet another embodiment, the adenoviral vector carries more than one heterologous expression cassette, which can be inserted into multiple deletion sites in the adenoviral genome. In this embodiment, the heterologous expression cassette can express the same or different products from multiple locations in the adenoviral genome.

1. The Nucleic Acid Sequence

The expression cassette contains a nucleic acid sequence, heterologous to the vector sequences flanking the sequence, which encodes a polypeptide, protein, or other product, of interest. Suitably, this product is immunogenic or antigenic. The nucleic acid coding sequence is operatively linked to regulatory components in a manner which permits transcription, translation, and/or expression of the product in a host cell. Suitable nucleic acid sequences and products may be readily selected by one of skill in the art. The selection of these elements is not a limitation of this invention.

2. Regulatory Elements

In addition to the major elements identified above for the expression cassette, the vector also includes conventional control elements which are operably linked to the sequences encoding the product in a manner that permits transcription, translation and/or expression of the product in a cell infected with the virus used in the invention. As used herein, "operably linked" sequences include both expression control sequences that are contiguous with the product (e.g., gene) of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer and/or CMV intronic region) [see, e.g., Boshart et al, *Cell*, 41:521-530 (1985)], the SV40 promoter, the dihydrofolate reductase promoter, the β-actin promoter an its variants, the phosphoglycerol kinase (PGK) promoter, and the EF1α promoter [Invitrogen]. In one embodiment, in which the antigen is a severe acute respiratory syndrome (SARS) coronavirus antigen, the β-actin promoter is used in combination with an enhancer and intron regions from CMV.

In another embodiment, the native promoter for the gene will be used. The native promoter may be preferred when it is desired that expression of the product should mimic native expression. The native promoter may be used when expression of the product must be regulated temporally or developmentally, in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the expression cassette includes a nucleic acid sequence encoding a product operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al., *Nat. Biotech.*, 17:241-245 (1999)). Other examples of promoters that are tissue-specific are known for liver [albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)], bone osteocalcin [Stein et al., *Mol. Biol. Rep.*, 24:185-96 (1997)]; bone sialoprotein [Chen et al., *J. Bone Miner. Res.*, 11:654-64 (1996)], lymphocytes [CD2, Hansal et al., *J. Immunol.*, 161:1063-8 (1998); immunoglobulin heavy chain; T cell receptor chain], neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgfgene (Piccioli et al., *Neuron*, 15:373-84 (1995)), among others.

Optionally, vectors carrying sequences encoding immunogenic products may also include selectable markers or reporter genes may include sequences encoding geneticin, hygromycin or puromycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements is conventional for those of skill in the art and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

As stated above, while in one embodiment the immunization regimen of the invention involves sequential delivery of the same immunogenic product via different viral vectors, the heterologous expression cassette(s) used in the vectors of any given regimen need not be the same. In fact, each heterologous expression cassette can contain regulatory sequences for the immunogenic product and/or vector elements which differ from the regulatory sequences and vector element in other expression cassettes used in the regimen. Thus, the selection of these regulatory and vector elements is not a limitation of the invention, even within the context of an immunization regimen for a selected subject.

II. Adenoviral Particles

A variety of production methods for adenoviral particles is known to those of skill in the art. The selection of appropriate production methods is not a limitation of the present invention. See, e.g., U.S. Pat. No. 6,083,716; International Patent Publication No. WO 02/33645; and U.S. patent application Ser. No. 10/465,302, which are incorporated by reference. Briefly, production of an adenoviral vector lacking the ability to express one or more essential adenoviral products (e.g., E1a, E1b, E2a, E2b, E4 ORF6, L1, L2, L3, L4 and L5) can be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) and/or a packaging host cell. See, for example, the techniques described for preparation of a "minimal" human Ad vector in International Patent Publication No. WO96/13597, published May 9, 1996, and incorporated herein by reference.

Regardless of whether the adenoviral vectors contains only the minimal Ad sequences, or the entire Ad genome with only functional deletions in the E1, E3, and/or E4 regions, in one embodiment, the recombinant virus contains a capsid derived from a single adenovirus. Alternatively, in other embodiments, recombinant pseudotyped adenoviruses or hybrid adenoviruses may be used in the methods of the invention. Methods for producing these adenoviral vectors have been described.

A. Helper Viruses

Thus, depending upon the adenovirus gene content of the viral vectors employed to carry the expression cassette, a helper adenovirus or non-replicating virus fragment may be necessary to provide sufficient adenovirus gene sequences necessary to produce an infective recombinant viral particle containing the expression cassette. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264:16985-16987 (1989); K. J. Fisher and J. M. Wilson, *Biochem. J*, 299:49 (Apr. 1, 1994). Helper virus may optionally contain a second reporter expression cassette. A number of such reporter genes are known to the art. The presence of a reporter gene on the helper virus which is different from the gene product on the adenovirus vector allows both the Ad vector and the helper virus to be independently monitored. This second reporter is used to enable separation between the resulting recombinant virus and the helper virus upon purification.

B. Complementation Cell Lines

To generate recombinant adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human adenovirus E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line that expresses the E1 gene products can be utilized for production of an E1-deleted simian adenovirus. Such cell lines have been described. See, e.g., U.S. Pat. No. 6,083,716.

One may utilize the sequences provided herein to generate a packaging cell or cell line that expresses, at a minimum, the adenovirus E1 gene under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired Ad gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant adenovirus E1 deleted vectors. Additionally, or alternatively, the invention provides cell lines expressing one or more simian adenoviral gene products, e.g., E1a, E1b, E2a, and/or E4 ORF6, that can be constructed using essentially the same procedures for use in the generation of recombinant simian viral vectors. Such cell lines can be utilized to transcomplement adenovirus vectors deleted in the essential genes that encode those products. The preparation of a host cell according to this invention involves techniques such as assembly of selected DNA sequences. This assembly may be accomplished utilizing direct cloning techniques. Such techniques have been described [G. Gao et al, *Gene Ther.* 2003 October; 10(22):1926-1930; US Patent Publication No. 2003-0092161-A, published May 15, 2003; International Patent Application No. PCT/US03/12405]. Alternatively, techniques such as cDNA and genomic cloning, which are well known and are described in Sambrook et al., cited above, and use of overlapping oligonucleotide sequences of the adenovirus genomes, combined with polymerase chain reaction, synthetic methods, and any other suitable methods which provide the desired nucleotide sequence can be used.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther,* 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

C. Assembly of Viral Particle and Transfection of a Cell Line

Generally, when delivering the vector comprising the expression cassette by transfection, the vector is delivered in an amount from about 5 µg to about 100 µg DNA, or about 10 to about 50 µg DNA to about $1\times10^4$ cells to about $1\times10^{13}$ cells, or about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Furthermore, the promoters for each of the adenoviral genes may be selected independently from a constitutive promoter, an inducible promoter or a native adenoviral promoter. The promoters may be regulated by, for example, a specific physiological state of the organism or cell (i.e., by the differentiation state or in replicating or quiescent cells) or by exogenously-added factors, for example. Introduction of the molecules (e.g., plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired expression cassette-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in recombinant viral vector particles. The current method for producing such virus particles is transfection-based. However, the invention is not limited to such methods.

The resulting recombinant viruses are useful in transferring a selected transgene to a selected cell.

III. MV Vectors

In one embodiment, the AAV vectors useful in the invention contain, at a minimum, sequences encoding an AAV capsid in which is packaged a heterologous expression cassette. The cassette is flanked by AAV 5' ITR and AAV 3' ITR. The AAV ITRs may be from the same source as the capsid, or from a different source (i.e., a pseudotyped AAV vector).

In one aspect, the invention provides a method of generating a recombinant adeno-associated virus (AAV). Such a method involves culturing a host cell which contains a nucleic acid sequence encoding an adeno-associated virus (AAV) capsid protein, or fragment thereof, as defined herein; a functional rep gene; an expression cassette flanked by, at a minimum, AAV inverted terminal repeats (ITRs); and sufficient helper functions to permit packaging of the expression cassette into the AAV capsid.

The components required to be cultured in the host cell to package an expression cassette flanked by AAV ITRs in an AAV capsid may be provided to the host cell in trans. Alternatively, any one or more of the required components (e.g., expression cassette, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the sequences encoding the product. In still another alternative, a selected stable host cell may contain selected component(s) under the control of a constitutive promoter and other selected component(s) under the control of one or more inducible promoters. For example, a stable host cell may be generated that is derived from 293 cells (which contain E1 helper functions under the control of a constitutive promoter), but which contains the rep and/or cap proteins under the control of inducible promoters. Still other stable host cells may be generated by one of skill in the art.

The expression cassette, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.,* 70:520-532 (1993) and U.S. Pat. No. 5,478,745.

Unless otherwise specified, the AAV ITRs, AAV capsids, and other selected AAV components described herein, may be readily selected from among any AAV serotype, including, without limitation, AAV1 [International Patent Publication No. WO 00/28061], AAV2, AAV3, AAV4, AAV5, AAV6, AAV7, AAV8, AAV9 and one of the other AAV described in International Patent Publication No. WO 2003/042397, U.S. Patent Application No. 60/508,226 and its international counterpart PCT/US04/028817, and U.S. Patent Application No. 60/669,083, entitled "Method of Increasing the Function of an AAV Vector", filed Apr. 7, 2005, which are incorporated by reference herein. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., the GenBank™ database, PubMed™ database, or the like.

The AAV vectors useful in the invention include vectors in which all AAV sequences and capsid proteins (e.g., fiber, penton, hexon) are derived from a single source. Alternatively, AAV vectors used in the invention include those that are trans-encapsidated (i.e., contain an AAV capsid of a different source than the AAV ITRS and/or other AAV elements in the capsid). Such trans-encapsidated vectors include those that are pseudotyped using conventional techniques, or that contain synthetic, artificial and/or chimeric capsids. See, e.g., International Patent Publication No. WO 2003/042397; U.S. Patent Application No. 60/508,226 and its international counterpart PCT/US04/028817, and U.S. Pat. No. 6,491,907].

In one embodiment, the invention utilized AAV viral vectors in which one or more of the vp1, vp2 and/or vp3 proteins (which assemble to form an AAV capsid) is modified in order to enhance antigenicity of the AAV, e.g., by increasing vector uptake by and activation of antigen presenting cells (APCs), dendritic cells, or another target cell or tissue type. The modified vp1, vp2 or vp3 protein assembles into an AAV capsid having the inserted peptide or protein exposed on the outer surface of the capsid. These modifications may be made using the methods of Girod et al, [A. Girod, et. al., *Nat Med,* 5(9): 1052-1056 (1999)] or Warrington et al, [K H. Warrington, Jr., et. al., *J. Virol.,* 78(12):6595-6609 (2004)]. According to the methods of Girod, a site in the vp3 coding domain of a selected AAV can by modified by inserting nucleic acid sequences at the coding region corresponding to amino acid position 587 of AAV2 [and in the corresponding sequence of other AAVs, as determined upon alignment using conventional programs and methods]. Such an amino acid insert may be from about 1 to 34 amino acids in length and may provide the assembled AAV capsid containing the modified AAV vp2 protein with a desired peptide, e.g., a peptide specific receptor, antigen, or another desirable sequence. Examples of suitable fragments include, e.g., peptides targeted to dendritic cells, such as DC3, DC12, and DC18 those described in T. J. Curiel, et al., *J. Immunol,* 172 (120):7425-31 (2004).

According to the methods of Warrington, the N-terminus of the vp2 capsid (i.e., position 138 of AAV2 and corresponding positions in other AAV sequences) can be modified to contain an insertion of a peptide, resulting in a fusion protein useful in the assembled AAV capsid containing the modified capsid protein. In one embodiment, these fusion proteins confer additional targeting sequences. In other embodiments, the fusion proteins may provide additional antigenic sequences. In one embodiment, insertions of up to 250 amino acids, more desirably 150 amino acids, or of lengths from 5 to 150 amino acids are selected. Examples of suitable sources of peptides include fragments obtained from, e.g., flagellin, heat shock protein, and complement proteins (such as complement component 3, fragment d).

It will be understood that still other AAV vectors may be selected for use in the present invention without limitation as to the origin of the capsid and/or the source of the AAV ITRs or other AAV elements.

A. The Packaging Expression Cassette

A heterologous expression cassette as defined above in connection with the adenoviral vectors useful in the invention is located between, at its 5' end, 5' AAV inverted terminal repeats (ITRs) and, at its 3' terminus, 3' AAV ITRs. Other AAV or vector elements may also be located between the expression cassette and ether the 5' AAV ITRs or the 3' AAV ITRs. It is this construct that is packaged into a capsid protein to provide an AAV vector of the invention.

The elements of the heterologous expression cassette, including the nucleic acid sequences encoding the product, the vector elements, and the like, are readily selected from among those described above of the adenoviral vector.

In one embodiment, the heterologous expression cassette delivered via rAAV according to the invention contains the immunogenic product operably linked to an inducible or regulatable promoter. When used in a regimen according to the present invention, the inducing or regulating agent is typically administered such that expression of product is activated immediately following administration of the rAAV. Thereafter, expression can be extinguished by removal of the inducing or regulating agent. The regimen of the invention can include "pulse" activation of expression. In other words, expression can be induced, extinguished, and then again induced after a period of time.

Inducible and regulatable promoters allow regulation of gene expression and can be regulated by exogenously supplied compounds, environmental factors such as temperature, or the presence of a specific physiological state, e.g., acute phase, a particular differentiation state of the cell, or replication. Regulatable promoters and systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], and the tetracycline-inducible system [Gossen et al, *Science*, 268-1766-1769 (1995), see also Harvey et al, *Curr. Opin. Chem. Biol.*, 2:512-518 (1998)]. Other systems include the FK506 dimer, VP16 or p65 using castradiol, diphenol murislerone, the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Post-transcriptional Regulatory Element (WPRE). Selection of the regulatable promoter is not a limitation of the present invention.

Further, the method of the invention is not limited to use of such promoters, and the heterologous expression cassettes carried by the rAAV according to the method of the invention can include constitutive, native, or tissue-specific promoter. Selection of this promoter is not a limitation on the present invention.

B. Rep and Cap Sequences

In addition to the minigene, the host cell contains the sequences which drive expression of an AAV capsid protein of the invention (or a capsid protein comprising a fragment thereof) in the host cell and rep sequences of the same serotype as the serotype of the AAV ITRs found in the minigene, or a cross-complementing serotype. The AAV cap and rep sequences may be independently obtained from an AAV source as described above and may be introduced into the host cell in any manner known to one in the art as described above. Additionally, when pseudotyping an AAV vector in (e.g., an AAV9/HU.14 capsid), the sequences encoding each of the essential rep proteins may be supplied by different AAV serotypes (e.g., AAV1, AAV2, AAV3, AAV4, AAV5, AAV6, AAV7, AAV8, AAV9, or any of the serotypes identified herein). For example, the rep78/68 sequences may be from AAV2, while the rep52/40 sequences may be from AAV8.

In one embodiment, the host cell stably contains the capsid protein under the control of a suitable promoter, such as those described above. In one embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. When delivered to the host cell in trans, the plasmid carrying the capsid protein may also carry other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

The promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions are supplied by a herpesvirus. The necessary helper functions may each be provided from a human or non-human primate adenovirus source, such as those described above and/or are available from a variety of sources, including the American Type Culture Collection (ATCC), Manassas, Va. (US). In yet another embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In still another embodiment, no other adenovirus genes or gene functions are present in the host cell.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

D. Host Cells and Packaging Cell Lines

The host cell itself may be selected from any biological organism, including prokaryotic (e.g., bacterial) cells, and eukaryotic cells, including, insect cells, yeast cells and mammalian cells. In one embodiment, host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4ORF6; it not contain any other virus gene which could result in homologous recombination of a contaminating virus during the production of rAAV; and it is capable of infection or transfection of DNA and expression of the transfected DNA. In a one embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another host cell contains the minimum adenoviral DNA which is sufficient to express E4ORF6. Yet other cell lines can be constructed using the novel AAV9 cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

Thus, the invention further provides vectors useful in the vaccine/immunization regimens described herein. These, or other AAV vector constructs may be used in regimens for delivery of an immunogen in a regimen involving sequential administration of Ad vectors.

IV. Immunization Regimens

According to the present invention, recombinant vectors are used in the immunization regimen of the invention for inducing an immune response in a human or non-simian veterinary patient following ex vivo or in vivo administration. In one embodiment, the immune response induced is a humoral (i.e., antibody) response to the product expressed by the viral vectors. Depending upon the antigen product expressed, such an antibody response can be specific to the pathogen from which the antigen is derived or cross-reactive with other, related pathogens. In another embodiment, the immune response can be a cellular (e.g., CTL) response. Depending upon the immunogenic product expressed, such a CTL response can be specific to the pathogen from which the immunogen is derived or cross-reactive with other, related pathogens. In still other embodiments, both antibody and CTL response may be induced. However, the method of the invention is advantageous is that it minimizes, and in some cases eliminates, immune response to the viral vector, and particularly, the adenoviral vector.

Thus, the immunization regimens of the invention can be applied either in prophylactic or therapeutic vaccines. Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a composition of the invention may be formulated to contain viral vectors as described herein, as well as other components, including, e.g. adjuvants, stabilizers, pH adjusters, preservatives and the like. Suitable exemplary preservatives include chlorobutanol, potassium sorbate, sorbic acid, sulfur dioxide, propyl gallate, the parabens, ethyl vanillin, glycerin, phenol, and parachlorophenol.

Suitable chemical stabilizers include gelatin and albumin. Suitable exemplary adjuvants include, among others, immune-stimulating complexes (ISCOMS), LPS analogs including 3-O-deacylated monophosphoryl lipid A (Ribi Immunochem Research, Inc.; Hamilton, Mont.), mineral oil and water, aluminum hydroxide, Amphigen, Avirdine, L121/squalene, muramyl peptides, and saponins, such as Quil A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming adenoviral vector.

The viral vectors used in the invention are administered in "an immunogenic amount", that is, an amount of virus that is effective in a route of administration to transfect the desired cells and provide sufficient levels of expression of the selected gene to induce an immune response. Where protective immunity is provided, the viruses are considered to be vaccine compositions useful in preventing infection and/or recurrent disease.

Alternatively, or in addition, the vectors used in the invention may contain nucleic acid sequences encoding a product (e.g., a peptide, polypeptide, or protein) which induces an immune response to a selected immunogen. The immunogenic regimen provided herein is expected to be highly efficacious at inducing cytolytic T cells and antibodies to the inserted heterologous antigenic protein expressed by the vector.

Immunogens may be selected from a variety of viral families. Example of viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses.

Other target antigens may be generated from the Hepatitis C [see, e.g., US Published Patent Application No. US 2003/190606 (Oct. 9, 2003); US 2002/081568 (Jun. 27, 2002)] or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutinelterose) glycoprotein (not present in all coronaviruses), or N (nucleocapsid). The coronavirus family includes the putative causative agent for sudden acute respiratory syndrome (SARS). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (e.g., the glyco-(G) protein and the fusion (F) protein, for which sequences are available from GenBank).

The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp140, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, J. Virol., 75(5):2462-2467 (March 2001), and R. R. Amara, et al, Science, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins has been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Additional sources of target antigens and immunogens are discussed in more detail below.

The papovavirus family includes the sub-family polyomaviruses (BKU and JCU viruses) and the sub-family papillomavirus (associated with cancers or malignant progression of papilloma). Examples of papillomavirus proteins useful as immunogenic products include those derived from the papilloma virus "early" and "late" genes designated E1 to E7, L1 and L2. See, e.g., US Published Patent Application No. 2002/0137720 [Ertl]. Other papillomavirus antigens and combinations thereof have been described. See, e.g., US Published Application No. 2003/129199 (Jul. 10, 2003); US Published Application No. 2002/18221 (Dec. 15, 2002); U.S. Pat. No. 6,342,224.

The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (Human CMV), muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass regimens utilizing product which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and *eikenella; melioidosis; salmonella; shigella; haemophilus* (*Haemophilus influenzae, Haemophilus somnus*); *moraxella; H. ducreyi* (which causes chancroid); brucella; *Franisella tularensis* (which causes tularemia); *yersinia* (pasteurella); *streptobacillus moniliformis* and *spirillum*. Gram-positive bacilli include listeria monocytogenes; erysipelothrix rhusiopathiae; *Corynebacierium diphtheria* (*diphtheria*); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria.

Examples of specific bacterium species are, without limitation, *Streptococcus pneumoniae, Streptococcus pyogenes, Streptococcus agalactiae, Streptococcus faecalis, Moraxella catarrhalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium, Mycobacterium intracellulare complex, Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum.*

Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis (*Cryptococcus*), blastomycosis (*Blastomyces*), histoplasmosis (*Histoplasma*) and coccidioidomycosis (*Coccidiodes*); candidiasis (*Candida*), aspergillosis (*Aspergillis*), and mucormycosis; sporotrichosis; paracoccidiodomycosis, petriellidiosis, torulopsosis, mycetoma and *chromomycosis*; and dermatophytosis. Rickettsial infections include Typhus fever, Rocky Mountain spotted fever, Q fever, and Rickettsialpox. Examples of mycoplasma and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis (e.g., caused by *Leishmania major*); trypanosomiasis; toxoplasmosis (e.g., caused by

*Toxoplasma gondii*); *Pneumocystis carinii; Trichans; Toxoplasma gondii*; babesiosis; giardiasis (e.g., caused by *Giardia*); trichinosis (e.g., caused by Trichomonas); filariasis; schistosomiasis (e.g., caused by *Schistosoma*); nematodes; trematodes or flukes; and cestode (tapeworm) infections. Other parasitic infections may be caused by *Ascaris, Trichuris, Cryptosporidium*, and *Pneumocystis carinii*, among others.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella* tularensis (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors according to the invention to deliver immunogens against the variable region of the T cells elicit an immune response including CTLs to eliminate those T cells. In rheumatoid arthritis (RA), several specific variable regions of T-cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant simian adenovirus that encodes at least one of these polypeptides will elicit an immune response that will target T cells involved in scleroderma.

Further, desirable immunogens include those directed to eliciting a therapeutic or prophylactic anti-cancer effect in a vertebrate host, such as, without limitation, those utilizing a cancer antigen or tumor-associated antigen including, without limitation, prostate specific antigen, carcino-embryonic antigen, MUC-1, Her2, CA-125 and MAGE-3.

Suitably, the adenoviral vectors and AAV vectors are delivered in a combination regimen involving sequential administration, or coadministration, of an adenoviral vector and an AAV vector. These regimens can further include sequential or coadministration administration with one or more additional adenovirus vectors, e.g., a functionally E1-deleted, functionally E4-deleted adenovirus, one or more additional AAV vectors, or other therapeutic and/or vaccine agents.

In one embodiment, the regimen further involves administration of a DNA vaccine, e.g., via gene gun or plasmid. Such a DNA vaccine may be used as a priming step, which precedes adenoviral-mediated and/or AAV-mediated delivery according to the invention. Alternatively, such a DNA vaccine may be used as a boost following one or more adenoviral-mediated and/or AAV-mediated delivery of the invention.

In another embodiment, the regimen further involves sequential or co-administration of a protein-based vaccine. Such a vaccine can be used as a boost, following adenoviral-mediated and/or AAV-mediated delivery according to the invention. Alternatively, such a protein-based vaccine may be used as a prime, or in between one or more adenoviral-mediated and/or AAV-mediated immunizations in a regimen of the invention.

In one example, an immunization regimen of the invention provides a protective immune response to the virus, bacteria or other organism, from which the antigen is derived, or a cross-reactive virus, bacteria or other source. In another example, the immunization regimen described herein can include a multiprotein regimen. See, e.g., R. R. Amara, *Science,* 292:69-74 (6 Apr. 2001) which describes a multiprotein regimen for expression of protein subunits useful for generating an immune response against HIV and SIV.

In another desired embodiment, the regimen provides a therapeutic immune effect. Optionally, these effects can be measured using assays for detection of the presence of antigen-specific antibodies, T cells, or the condition for which therapy is being administered.

The vectors used in an immunization regimen of the invention can be administered at various sites in the body in a dose dependent manner, which depends on the product to which the desired immune response is being targeted. The invention is not limited to the amount or situs of injection(s) or to the pharmaceutical carrier. Rather, the regimen may involve a priming and boosting step, each of which may include a single dose or dosage that is administered hourly, daily, weekly or monthly, or yearly. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions used in the invention are administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Dosages of the viral vector will depend primarily on factors such as the condition being treated, the age, weight and health of the patient, and may thus vary among mammalian (including human) patients. Advantageously, the unexpected potency of the recombinant simian (e.g., chimpanzee) adenoviruses of the invention permits the use significantly lower amount of the recombinant chimpanzee adenovirus to provide an effective amount to induce the desired immunogenic effect (e.g., induction of a predetermined level of antibodies and/or CD8+ T cells).

For example, for small animals, an effective dose of an adenoviral vector may be provided by $10^5$ particles/animal and $10^{11}$ particles/animal of adenovirus. For a larger animal, e.g., about 80 kg, $10^7$ to about $10^{13}$ particles per subject may be useful. However, higher doses may be readily selected, e.g., depending upon the selected route of delivery. For example, the adenoviral vector may be delivered in an amount which ranges from about 100 μL to about 100 ml, and more preferably, about 1 mL to about 10 mL, of carrier solution.

In one embodiment, an effective dosage of the AAV vector is generally in the range of from about 0.1 ml to about 100 ml of solution containing concentrations of from about $1 \times 10^9$ to $1 \times 10^{16}$ genomes virus vector. A preferred human dosage for delivery to large organs (e.g., liver, muscle, heart and lung) may be about $5 \times 10^{10}$ to $5 \times 10^{13}$ AAV genomes per 1 kg, at a volume of about 1 to 100 mL. A preferred dosage for delivery to eye is about $5 \times 10^9$ to $5 \times 10^{12}$ genome copies, at a volume of about 0.1 mL to 1 mL.

Depending upon the desired routes of administration, one of skill in the art can select an appropriate regimen. In general, a second, or subsequent immunization, composition can be administered about 2 to about 27 weeks after administering the preceding immunization composition, to the mammalian subject. The administration of the subsequent composition is accomplished using an effective amount of a composition containing or capable of delivering the same antigen as administered by the prior composition. Desirably, the product of the boosting composition is the same, or cross-reactive, as that encoded by the priming composition.

The time period between sequential administrations, according to the present invention, can be adjusted according to the order of Ad-mediated delivery, AAV-mediated delivery, and any optional additional priming or boosting compositions (e.g., DNA-based or protein-based vaccines). For example, peak immune response is generally observed about 10 to 14 days following an Ad-mediated delivery. However, boosting following this peak may generate a second peak. Thus, it may be desirable to time expression of a boosting antigen to express from about 10 to 21 days, or 18 to 28 days, or 28 days to 27 weeks following Ad-mediated delivery. In another example, certain AAV serotypes demonstrate peak expression about 3 to 4 weeks following delivery. Thus, boosting following AAV delivery may be timed to express the antigen, or a cross-reactive antigen, about 3 weeks to about 4 weeks, about 4 weeks to about 2 months, or about 2 months to 27 weeks months, or longer, following AAV delivery.

In one embodiment, the heterologous expression cassette delivered via a viral vector, e.g., an AAV vector, according to the invention contains the immunogenic product operably linked to an inducible or regulatable promoter. When used in a regimen according to the present invention, the inducing or regulating agent is typically administered such that expression of product is activated immediately upon administration of the viral vector. Thereafter, expression can be extinguished by removal of the inducing or regulating agent. The regimen of the invention can include "pulse" activation of expression. Thus, the method of the invention permits expression to be induced, extinguished, and then again induced after a period of time. In another embodiment, expression is induced not upon administration, but several days to several weeks following administration. This embodiment may permit co-delivery of an Ad and AAV followed by induction (activation) several weeks following delivery, depending upon the delay caused by the induction agent. For example, once an inducing agent is delivered, it may be 7 to 10 days or longer before the effect is observed. One of skill in the art will be familiar with the delay between delivery of the inducing or activating agent and the effect and will be able to readily factor this into the selected regimen.

The therapeutic levels or levels of immunity, of the selected gene can be monitored to determine the need, if any, for boosters. Following an assessment of CD8+ T cell response, or, antibody titers, in the serum, optional additional booster immunizations may be desired.

In another aspect, the invention provides a product useful for performing the immunization regimens described herein.

Such a product can contain one or more of the adenoviral vectors described herein in a suitable container. Typically, such a product will further contain instructions for administration of the adenoviral vectors.

Further, the product may contain a physiologically acceptable carrier suitable for the selected route of delivery, e.g., for dilution and/or reconstitution of one or more the adenoviral vectors, syringes, vials, and the like.

EXAMPLES

The following examples are provided to illustrate the invention and do not limit the scope thereof. One skilled in the art will appreciate that although specific reagents and conditions are outlined in the following examples, modifications can be made that are meant to be encompassed by the spirit and scope of the invention.

Recently, a strategy involving sequential immunizations with heterologous vaccine carriers expressing the same antigen has resulted in the generation of unparalleled levels of specific immunity and, in some cases, afforded protection against infectious agents.

Replication-defective, adenoviral vectors based on human serotype 5 (H5) can induce robust cellular and humoral immune responses against the transgene product. In addition, adeno-associated viral (AAV) vectors have also been shown to elicit antigen-specific immune responses.

Example 1

For the studies described in Example 2, Ebola Zaire virus envelope glycoprotein (Ebo GP) was used as a model antigen to create H5CMVGP and AAV-1CMVGP vaccine vectors. AAV serotype I was chosen because it is highly efficient in transducing muscle.

The vectors used in these studies were generated using conventional methods, as follows.

A. Generation of Adenoviral Vector

1. Creation of Molecular Clones of EboZ Expressing Adenovirus Vectors

Recombinant adenovirus genomes that derived from different species and strains of adenoviruses and express EboZGP were created through direct ligation and green/white selection system that was described elsewhere [Gao et al., Gene Therapy, 2003 and Roy et al., Human Gene Therapy, 15(5):519-530 (May 2004)]. Briefly, the EboZGP cDNA was subcloned into a universal pShuttle plasmid vector between CMV promoter and bovine growth hormone poly A which was used for introducing the EboZGP into a variety of molecular clones of adenovirus backbones.

The molecular clones of adenovirus backbones include Human serotype 5 with E1 and E3 deletions (H5.040), Chimpanzee serotype 7 with E1 deletion only (C7.000), E1 and E3 deletions (C7.010) and E1 and E4 deletions (C7.001). The cloning process to create those molecular clones were described elsewhere [Gao et al., Gene Therapy, cited above, 2003 and Roy et al., Human Gene Therapy, 15(5):519-530 (May 2004)]. All these molecular clones containing a cassette that expressed prokaryotic GFP from bacterial lac promoter and flanked by two rare restriction sites, PI-Sce I and I-Ceu I. This allowed the EboZ expression cassette from the universal pShuttle construct to be swapped into the adenovirus molecular clones through a convenient and efficient green/white selection mediated cloning process (Gao et al., Gene Therapy, 2003).

2. Rescue, Expansion and Purification of AdEboZ Vectors

To rescue recombinant viruses from the molecular clones, the plasmid DNAs were linearized by appropriate restriction enzymes to release the vector genomes from plasmid backbones and transfected into appropriate cell lines. For E1/E4 deleted vectors, 10-3 cells, a 293 cell based E1/E4-complementing cell line with E4ORF6 expressed under Zinc induction were used. For all other constructs, 293 cells were used.

Once full cytopathic effect (CPE), the sign of virus rescue and replication, was observed, crude viral lysate harvested for gradual expansion to large scale infections in appropriate cell lines. Viruses were purified by the standard CsCl gradient sedimentation method. The genome structures of recombinant viruses were confirmed by restriction enzyme analysis. For all vector except for E1/E4-deleted vectors, infectivity of the viruses were determined by plaque assay on 293 cells. However, the vectors used for immunization experiments were dosed based on virus physical particle numbers measured by $OD_{260}$ readings on a UV-spectrophotometer.

B. Creation and Production of MV2/1CMVEboZGP Vector

To create the recombinant AAV2 genome expressing EboZ glycoprotein, the EGFP insert in pAAV2CMVEGFP plasmid [E. M. Surace et al, J. Virol., 77(14):7957-7963 (July 2003) was replaced with the EboZGP cDNA.

Recombinant AAV2/1CMVEboZGP virus was produced by the triple transfection method in 293 cells to transencapsidate the AAV2CMVEboZGP genome with AAV1 capsids. The vector was purified by CsCl sedimentation method. The genome copy titer of the vector was determined by real time PCR, whereas its infectious titer was analyzed by the infectious center assay. The vector doses for vaccination were based on the genome titer.

Example 2

Immunization Regimen of Invention Boosts Immune Response to Antigen

Figure 1:
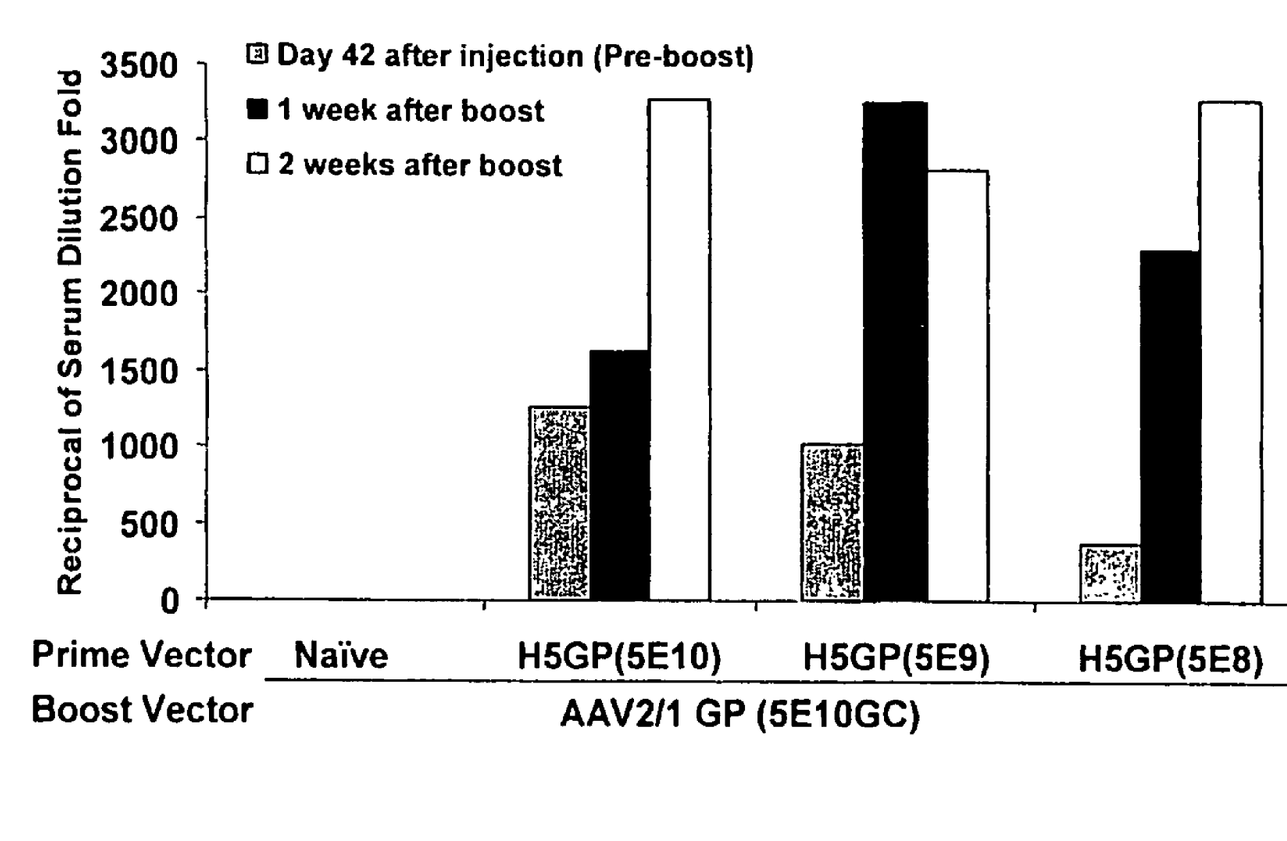

B10BR mice (6-8 weeks old) were purchased from The Jackson Laboratory (Bar Harbor, Me.) and kept at the Animal Facility of The Wistar Institute (Philadelphia, Pa.). Mice were immunized with recombinant adenoviral vectors or recombinant adeno-associated viral vectors diluted in 100 μl PBS at the doses provided below by intramuscular injection. More particularly, priming was with recombinant adenoviral vectors was at $5 \times 10^{10}$, $5 \times 10^9$, or $5 \times 10^8$ particles/mouse of H5GP vector. Boosting was with $5 \times 10^{10}$ genome copies/mouse of AAV2/1 GP vector. Serum from 3 mice in each group were collected and pooled at either day 42 after injection (pre-boost), or 1 week after boost, or 2 weeks after boost, as indicated in the FIGURE. Total IgG responses to GP were measured by ELISA.

A. Antigen-Specific Immune Response

GP-specific T cell and B cell responses elicited in B10BR mice were analyzed after vaccination by IM injection with either H5CMVGP or AAV-1CMVGP vectors alone.

The TELRTFSI [SEQ ID NO: I] peptide which carries the immunodominant MHC class I epitope of EboZ GP for mice of the $H-2^k$ haplotype was synthesized by Mimotopes (Victoria, Australia). Peptide was diluted in DMSO to a concentration of 5 mg/ml and stored at −80° C. Peptide was used at 2 μg/ml and DMSO concentrations were kept below 0.1% (v/v) in all final assay mixtures.

Splenocytes from immunized mice were stimulated with $H-2^K$ restricted EboZ GP-specific peptide (TELRTFSI, SEQ ID NO:1) for 5 hours at 37° C. and 10% $CO_2$ in the presence of 1 μl/ml Brefeldin A (GolgiPlug, BD PharMingen, San Diego, Calif.). Control cells were incubated without peptide. After washing, cells were stained with a FITC-labeled anti-mouse CD8 antibody (BD PharMingen). Then, cells will be washed and permeabilized in Cytofix/Cytoperm (BD PharMingen) for 20 minutes on ice. Subsequently, cells were washed again and stained with a PE-labeled anti-mouse IFN-γ antibody (BD PharMingen). After extensively washing, cells were examined by two-color flow cytometry and data were analyzed by WinMDi software. Splenoctyes incubated without the peptide to GP showed<0.5% IFN-gamma producing CD8+ T cells.

AAV-1CMVGP vectors at a dose of $5 \times 10^{10}$ genome copies per mouse induced much lower frequencies of $CD8^+$ T cell producing IFN-γ by intracellular cytokine staining with $H-2^k$ restricted GP-specific peptide as stimulant and less total IgG response to GP measured by ELISA than H5CMVGP at a dose of $5 \times 10^8$ particles per mouse.

B. Enhanced Immune Response to Antigen

Immune responses elicited in B10BR mice were examined after priming with H5CMVGP ($5 \times 10^8$ particles/mouse) and boosting with AAV-1CMVGP ($5 \times 10^9$ genome copies/mouse).

Mice were bled either by retro-orbital puncture at various times after immunization or by heart-puncture at the termination. Sera were prepared and tested for total IgG response to EboZ GP on 96-well plates coated with EboZ VLPs diluted in PBS. The plates were coated overnight at 4° C. and blocked for 2 hours with PBS containing 3% bovine serum albumin (BSA) at room temperature. After washing, sera diluted in PBS containing 1% BSA were added onto wells for 2 hours at room temperature. After washing, a 1:10,000 dilution of horseradish peroxidase-conjugated goat anti-mouse IgG (Sigma Chemicals, St. Louis, Mo.) was added to the wells for 1 hour at room temperature. After washing, TMB substrate (Sigma Chemicals) was added for 10-20 minutes and reaction was subsequently stopped by adding Stop Reagent (Sigma Chemicals). Optical density was red at 450 nm. A cut-off value for positive sample was calculated as the mean delta OD at 450 nm for naïve serum at a 1:100 dilution plus 3 times of standard deviations. The endpoint antibody titer of each sample tested was then defined as the reciprocal of the highest dilution of the serum with a delta OD at 450 nm, which was interpolated according to the linear regression analysis, above the cut-off value.

A significant increase of total IgO response against GP was observed as early as 10 days after boost. More important, the total IgG response against GP achieved by this prime/boost strategy was at least 2 to 4 fold higher than that generated by H5CMVGP alone even at a dose of 5×10$^{10}$ particles per mouse. See, FIG. 1.

Example 3

Immunization Against Ebola Using Capsid Modified Versions of AAV8 and Adenovirus Expressing Ebola Envelope Glycoproteins A. Generation of MV 8 with Insertion Cassettes Modified vp1 proteins having inserts at amino acid residue position 587 of AAV8 are being generated using a first class of peptides designed to increase dendritic cell (DC) transduction by the incorporation of known DC binding motifs. These peptides have been described [T. J. Curiel, et al., *J. Immunol.*, 172(12):7423-31 (2004)].

In order to make AAV more attractive as a vaccine carrier, we will attempt to enhance the ability of the capsid to activate innate immunity. A panel of selected molecules that have been described to enhance cellular immune responses, some of them in a known TLR dependent manner, will be fused to the AAV capsid. In this rationale the capsid will generate the proper inflammatory context for recruitment and activation of APCs. While the engineered capsid acts as a danger signal, the transgene expression will then act to prime the adaptive immune system.

| Class | Protein/peptide | #AA | Target cells |
|---|---|---|---|
| I | DC3 | 12 | DC |
| I | DC12 | 12 | DC |
| I | DC18 | 12 | DC |

Insertion in position 587 will be accomplished by insertional mutagenesis making use of splicing by overlap extension [Horton, R. M., et al., Gene, 1989, 77(10):61-68]. Two sets of primers will be designed that give rise to two fragments flanking the 587 insertion site. The insertion itself will be encoded on the 5' tail of the internal primers making sure that there is sufficient overlap for annealing in the splicing step. The external 2 primers will encode for the conserved BsiWI and EcoRV sites in the packaging plasmids p5E18 (AAV2), pAAV2/1 and pAAV2/8. In a second PCR reaction those two fragments will be spliced together in the presence of the two external primers and the two fragments. The spliced fragment will then be digested with BsiWI and EcoRV and subsequently ligated to the similarly digested paternal packaging vector to generate the trans plasmid pAAV2/8 (modified).

The AAV2/8 vector having the modified capsid is then generated using known methods. See, e.g., Example 1.

B. Generation of MV8 with VP2 Fusion Proteins

Fusion proteins using the class 1 molecules DC3, DC12 and DC18 will be generated using the methods described herein.

In addition, vp2 fusion proteins are being generated using a second class of molecules aimed at engaging the innate immune system through known receptor-ligand interaction. This process is expected to yield the pro-inflammatory milieu essential for a productive adaptive immune response. Whereas a strong pro-inflammatory response is undesirable for gene therapy, it is considered advantageous for vaccine purposes.

| Protein/Peptide | Common Name | Organism | #AA | Ligand | Target Cells |
|---|---|---|---|---|---|
| FlaA | Flagellin | L. monocytogenes | 287 | TLR5 | Mono DC |
| Hsp60 | Heat Shock Protein | Human | 573 | TLR4 | Mono DC |
| C3d | Complement Component 3 Fragment d | Human/Mouse | 294 | CD21 (CR2) | B cell fDCs |

AA: number of Amino Acids, RGD motif: a tripeptide motif Arg-Gly- Differentiation, (f)DC: (follicular) Dendritic Cell, Mono: Monocytes Asp supports cell adhesion through binding a subset of integrin molecules. TLR: Toll Like Receptor, CD: Cluster of differentiation.

The FlaA protein has been described [Hayashi, F., et al., Nature, 2001. 410(6832): p. 1099-103]. The Hsp60 protein has been described [Ohashi, K., et al., *J Immunol*, 2000. 164(2): p. 558-61]; the C3d protein has been described [D'Souza, S. E., et al., *Trends Biochem Sci*, 1991. 16(7): p. 246-50; M. C. Carroll, *Annu Rev Immunol*, 1998. 16: p. 545-68].

For the VP2 N-terminal fusion, a similar set of packaging plasmids described by Warrington et al., cited above, will be made for AAV8. A VP1,3 only expressing vector and a plasmid expressing VP2 from a mutated strong start ATG will be constructed as described by the authors. In short, for the VP1,3 expressing plasmid the VP2 start codon will be mutated by site directed mutagenesis into GCG coding for Alanine. The VP2 strong start plasmid (VP2A) will be obtained by subsequently mutating the VP1 and VP3 ATG into CTG followed by the introduction of ATG as the VP2 start.

In order to obtain a flexible system for insertions into position 138, a linker was introduced in the VP2A packaging plasmids. Making use of the Quickchange™ mutagenesis kit (Stratagene, La Jolla, Calif.) we will insert the unique NheI and ClaI sites right after the start codon of VP2 at AA position 138. All peptides can then be inserted by PCR from the cDNA making use of flanking primers encoding for the NheI (5') and ClaI (3') sites. In this way the peptides can be introduced in the different VP2A packaging plasmids in a uniform way.

The AAV2/8 vector having the modified capsid is then generated using these trans plasmids and known methods. See, e.g., Example 1.

C. Immunization Regimen with (A)

Animals are primed intramuscularly with an adenoviral vector, e.g., AdH5EboZ GP, at different doses. Six weeks later, animals are boosted with a modified AAV8 (having a vp1 insertion cassette, prepared as described in A) carrying EboZ GP at a dose of 5×10$^{10}$ genome copies per animal. GP-specific CD8$^+$ T-cell response and total IgG titer can be measured both before and after boost.

A significant increase in a GP-specific cellular immune response and/or an improved humor immune response.

D. Immunization Regimen with (B)

Animals are primed intramuscularly with an adenoviral vector, e.g., AdH5EboZ GP, at different doses. Six weeks later, animals are boosted with the modified AAV8 (having a vp2 fusion protein, prepared as described in step A) carrying the same antigen (EboZ GP) at a dose of 5×10$^{10}$ genome copies per animal. GP-specific CD8$^+$ T-cell response and total IgG titer can be measured both before and after boost.

A significant increase in GP-specific IgG titer by ELISA after boost is anticipated.

For the FlaA-containing modified AAV8 capsid, improved DC activation and improved Ag expressing transgene introduced into the antigen-presenting cell is anticipated.

For the hsp60 and C3d-containing modified AAV8 capsids, activation of innate immunity is anticipated.

All publications cited in this specification, and the sequence listing, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. An immunization regimen comprising delivering to a subject:
    (a) a replication-defective adenovirus comprising a first heterologous expression cassette comprising a nucleic acid sequence encoding a product for inducing an immune response to said product under the control of regulatory control sequences which direct expression of said product; and
    (b) an adeno-associated virus (AAV) comprising a second heterologous expression cassette comprising a nucleic acid sequence encoding said product for inducing an immune response to said product under the control of regulatory control sequences which direct expression of said product,
    wherein the AAV is delivered prior to delivery of the replication-defective adenovirus.

2. The regimen according to claim 1, wherein the regulatory sequences in the first and second expression cassettes of the replication-defective adenovirus and adeno-associated virus differ.

3. The regimen according to claim 1, wherein the regulatory sequences of the adeno-associated virus comprise an inducible promoter.

4. The regimen according to claim 3, further comprising delivering an inducing agent to the subject following administration of the AAV.

5. The regimen according to claim 4, wherein the inducing agent is administered to the subject following administration of the adenovirus.

6. The regimen according to claim 1, wherein the adenovirus further comprises a deletion in the region selected from the group of adenovirus regions consisting of E2, E3, E4, L1, L2, L3, L4, and L5 region.

7. The regimen according to claim 1, wherein the expression cassette of the adenovirus is located in site of an E1 region.

8. The regimen according to claim 1, wherein the first expression cassette of the adenovirus and/or the second expression cassette of the adeno-associated virus is located in an deleted E3 region.

9. The regimen according to claim 1, wherein the adenovirus is of a serotype selected from the group consisting of C5, C6, C7, C68 and C1.

10. The regimen according to claim 1, wherein the adenovirus is administered orally, intranasally, or intramuscularly.

11. The regimen according to claim 1, wherein the AAV is of a serotype selected from the group consisting of AAV1 and AAV8.

12. The regimen according to claim 1, wherein the AAV is administered intramuscularly.

13. The regimen according to claim 1, wherein the regimen further comprises administering a DNA vaccine.

14. The regimen according to claim 13, wherein said DNA vaccine is administered prior to the AAV vector.

15. The regimen according to claim 1, further comprising administering a protein-based vaccine.

16. The regimen according to claim 15, wherein said protein-based vaccine is delivered after the adenoviral vector.

17. The regimen according to claim 15, wherein said protein-based vaccine is delivered after the AAV vector.

18. The regimen according to claim 1, wherein the AAV vector has a modified capsid comprising a heterologous peptide or polypeptide that enhances antigenicity of the AAV vector.

19. The regimen according to claim 18, wherein the modified capsid comprises a vp2 protein having a peptide fused to its N-terminus.

20. The regimen according to claim 18, wherein the modified capsid comprises a modified vp1 protein having a peptide inserted therein.

21. A method of inducing an antigen-specific humoral or T-cell response in a subject, comprising administering:
    (a) a replication-defective adenovirus vector comprising a first heterologous expression cassette comprising a nucleic acid sequence encoding a product for inducing an antigen-specific humoral or T-cell response to said product under the control of regulatory control sequences which direct expression of said product; and
    (b) an adeno-associated virus (AAV) vector comprising a second heterologous expression cassette comprising nucleic acid sequence encoding said product for inducing an antigen-specific humoral or T-cell response to said product under the control of regulatory control sequences which direct expression of said product
    wherein said replication-defective adenovirus vector is administered after said adeno-associated virus (AAV) vector.

22. The method according to claim 21, further comprising administration of multiple adeno-associated virus (AAV) vectors before administration of said replication-defective adenovirus vector.

23. The method according to claim 21, further comprising administration of multiple replication-defective adenovirus vectors after said adeno-associated virus (AAV) vector.

* * * * *